United States Patent [19]

Taichi et al.

[11] Patent Number: 4,906,348

[45] Date of Patent: Mar. 6, 1990

[54] FLOW-THROUGH CELL PROVIDED WITH REFERENCE ELECTRODE

[75] Inventors: Yoshio Taichi; Ryuji Tao; Osamu Ohno, all of Katsuta, Japan

[73] Assignee: Hitachi, Ltd., Tokyo, Japan

[21] Appl. No.: 231,376

[22] Filed: Aug. 11, 1988

[30] Foreign Application Priority Data

Aug. 21, 1987 [JP] Japan .................. 62-206329

[51] Int. Cl.⁴ ............................................ G01N 27/46
[52] U.S. Cl. ................................ 204/409; 204/416; 204/435; 204/1 T
[58] Field of Search .............. 204/409, 416, 418, 419, 204/420, 435

[56] References Cited

U.S. PATENT DOCUMENTS

| | | | |
|---|---|---|---|
| 2,345,498 | 3/1944 | Perley | 204/435 |
| 3,658,679 | 4/1972 | Stansell et al. | 204/409 |
| 3,666,652 | 5/1972 | Krauer et al. | 204/409 |
| 4,544,455 | 10/1985 | Eisenhardt et al. | 204/435 |
| 4,714,527 | 12/1987 | Hofmeier et al. | 204/435 |

*Primary Examiner*—T. Tung
*Attorney, Agent, or Firm*—Fay, Sharpe, Beall, Fagan, Minnich & McKee

[57] ABSTRACT

A flow-through cell has a body under which an ion-selective electrode is disposed. The side portion of the cell body is provided with a reference electrode. The cell body has a sample path with a crank form and also has a substantially horizontally extended path for a reference electrode solution. The crank path has a lower horizontal part, so that it is possible to suppress the undesirable flowing down of the reference electrode solution into the ion-selective electrode during an ion concentration measurement operation. The crank path has a upper horizontal part, which serve to suppress the undesirable flowing of the blood cells contained in the blood sample towards the path for the reference electrode solution. Furthermore, the crank path for the sample is designed to suppress the occurrence of bubbles in the path, with the previso that, if such bubbles should occur, these bubbles may be smoothly withdrawn.

2 Claims, 1 Drawing Sheet

FLOW-THROUGH CELL PROVIDED WITH REFERENCE ELECTRODE

BACKGROUND OF THE INVENTION

The present invention relates to a flow-through cell provided with a reference electrode. Particularly, the invention relates to a flow-through cell suitable for measuring ions contained in a blood sample.

A combination of an ion-selective electrode and a reference electrode can be employed for measuring ions such as sodium, potassium, chloride ions, etc. contained in a blood sample. A flow-through cell, which has an open flow path, is so designed that a reference electrode solution flows into a path for a sample solution. In such a flow-through cell, a disturbance of the interface between the reference electrode solution and the sample solution often gives an adverse influence on the measurement of the ion concentration.

In H. F. Osswald et al, Chimia, 31 (1977), No. 2, there is disclosed a flow-through electrode, wherein a sample is flowed down through a vertical path and a reference electrode solution is flowed through a path which is narrower than the vertical sample path and then the reference electrode solution is delivered from an obliquely lower position to a middle part of the vertical sample path in order to suppress the disturbance of the interface between these two streams. However, this prior art has such a drawback that, since the electrode solution is passed through a narrow path, a number of bubbles stagnate on a connector member disposed between the solution reservoir and the narrow path, and a portion of the bubbles flow through the narrow path to the interface between the two streams. In addition, the narrow path is sometimes clogged with a particulate contaminant contained in the reference electrode solution. Therefore, the flow-through system according to Osswald et al. lacks a long term stability.

According to the prior art disclosed in Japanese Utility Model Patent Application (Laid-Open) No. 29759/1984, a valve is disposed in a path between a reference electrode and an ion-selective electrode, in order to suppress a disturbance of the interface between the two streams in question. However, in this prior art, the difference in specific gravity between the blood sample and the reference electrode solution may bring about an adverse effect on the interface stability.

Japanese Patent Application (Laid-Open) No. 169,756/1986 discloses a flow-through cell, wherein a sample path having a shape of circular loop is provided in the flow cell and a path for the reference electrode solution is connected to a middle portion of the loop path for the purpose of obtaining a stabilized potential between the two solutions. In this prior art, it is difficult to remove bubbles from the paths.

SUMMARY OF THE INVENTION

It is an object of the present invention to provide a flow-through cell which can generate a stable potential between a reference electrode solution and a sample solution and can eliminate any adverse influence caused by bubbles.

A flow-through cell according to the present invention has a cell body provided with a sample path which comprises a crank path consisting of an upper horizontal part, a lower horizontal part and a vertical part which communicates with the upper and lower horizontal parts. The sample flows from the bottom portion of the cell body to the upper portion of said body. A reference electrode is disposed at the side area of the cell body. There is provided a path for the reference electrode solution which extends from the reference electrode and opens at a middle portion of the vertical part of the crank path. The path for the reference electrode solution is substantially horizontal.

The flow-through cell according to the present invention has the above-mentioned structure, so that it is possible to prevent the undesired flowing down of the reference electrode solution to the ion-selective electrode disposed under the cell body, during the measurement time, and also to prevent the undesired flowing of the blood cells contained in the sample into the reference electrode during the measurement time. Since there are no bubble-stagnating portions in the crank path, it can be said that according to the present invention the adverse influence of bubbles on the measurement accuracy is neglible. Accordingly, the present invention has an advantage that there is less error of measurement of the concentration of ions in the sample.

DETAILED EXPLANATION OF THE PREFERRED EMBODIMENT

A detailed explanation is given below about a preferred embodiment of the present invention with reference to FIGS. 1 to 3.

Figure 1:
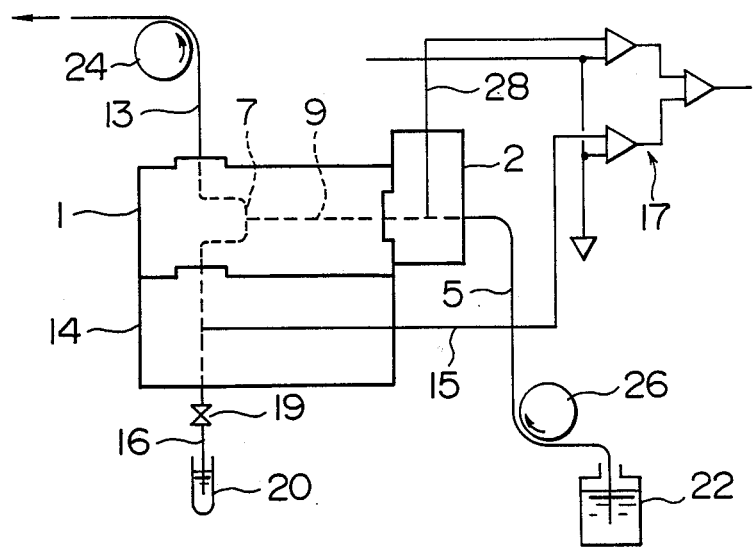
FIG. 1 is a schematic view of a flow-through cell according to an embodiment of the present invention.

In FIG. 1, the side area of a cell body 1 is connected with a reference electrode 2. The lower portion of the cell body 1 is connected to at least one of various ion-selective electrodes. In the embodiment shown in FIG. 1, the lower portion of the cell body 1 is connected to a potassium ion-selective electrode 14. A sample inlet tube 16 may be inserted into a sample container 20, wherein a blood sample is placed. By means of a liquid delivery pump 24, the sample is introduced through the sample inlet tube 16 into the flow-through cell. The sample is then passed through the potassium ion-selective electrode 14 and the cell body 1 and thereafter withdrawn through a sample outlet tube 13. A reference electrode solution is supplied from a reference electrode solution reservoir 22 through a reference electrode solution path 5 to a path disposed in a reference electrode 2. A signal line 15 of the potassium ion-selective electrode 14 and a signal line 28 of the reference electrode 2 are connected to an electric circuit 17, so that an electromotive force, which depends on the concentration of the potassium ions contained in the sample, can be obtained owing to the difference in electric potential between the two electrodes.

Figure 2:
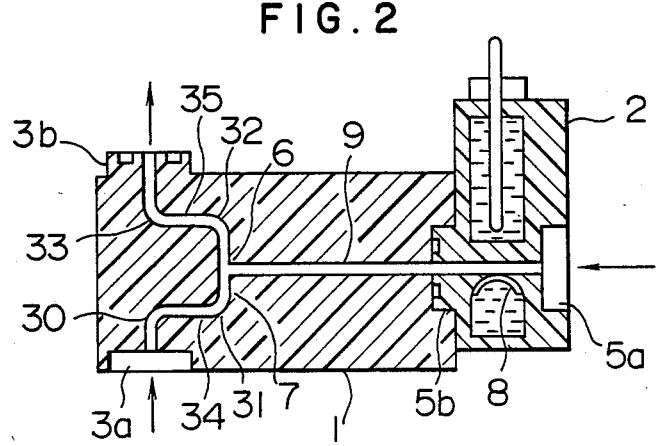
FIG. 2 is a cross-sectional view of the cell body area of the cell shown in FIG. 1.
Figure 3:
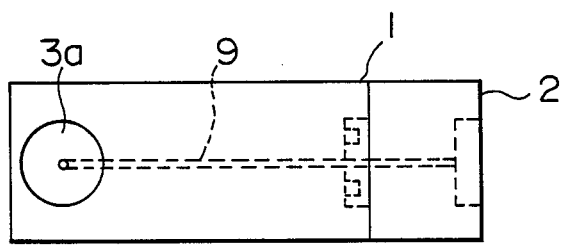
FIG. 3 is a bottom view of the cell body area shown in FIG. 2.

As shown in FIGS. 2 and 3, the reference electrode 2 employed is a liquid film type reference electrode containing an internal solution enclosed therein. The reference electrode 2 has a permeable membrane 8 and is connected via a connecting member 5b to the cell body 1. The reference electrode 2 is also connected at a path-connecting portion 5a to the path 5 by means of a connector. The cell body 1 is connected at a path-connecting portion 3a to the ion-selective electrode 14. Furthermore, the cell body 1 is connected at a path-connecting portion 3b to the sample outlet tube 13. One end of the sample path opens at the connecting portion 3a, and the other end of the sample path opens at the path-connecting portion 3b.

In the cell body 1, the sample path employed is a crank path. The crank path comprises an upper horizontal part 35, a lower horizontal part 34, and a vertical part 7 which communicates with both the two horizontal parts 34 and 35. Each of the turning portions of the crank path has a curved portion 30, 31, 32 or 33 to prevent any accumulation of bubbles in the turning portions. In a substantially middle portion of the vertical part 7, there is disposed an open end 6 of the path 9 for the reference electrode solution. The diameter of the sample path is virtually the same as that of the path 9 for the reference electrode solution. The lower horizontal part 34 of the crank path serves to suppress the undesired flowing of the reference electrode solution from the open end 6 into the ion-selective electrode during the measurement time.

An explanation is given below about the operation of the flow-through cell according to the above-mentioned embodiment of the present invention.

A human whole blood sample is placed in a sample cup 20. The valve 19 is opened, and then the blood sample flows by means of the pump 24 from the sample cup 20 through the sample inlet tube 16 to the sample path in the ion-selective electrode 14 and the cell body 1. When the sample path is filled with the blood sample, the pump 24 is stopped to terminate the of the blood sample. Thereafter, the valve 19 is closed, and the pumps 24 and 26 are started to pump the reference electrode solution through the path 9 to the outlet tube 13, whereupon an electromotive force, which depends on the concentration of potassium ions contained in the sample is generated in the electric circuit 17.

In this embodiment, it takes about 2 minutes as the interval time in the measurement operation of the concentration of potassium, sodium or chloride ions contained in the sample, by employing the combination of the ion-selective electrode and the reference electrode. The measurement time is less than 2 minutes, and a predetermined time is selected as the measurement time.

As the reference electrode solution, there is generally used a 1 mol aqueous potassium chloride solution. The specific gravity of the reference electrode solution is greater than that of the blood sample. If the sample path in the cell body 1 shown in FIG. 1 would be a straight vertical path, then it would be probable that a portion of the reference electrode solution flows down through the open end 6 of the path 9 and reaches the ion-selective electrode 14 within in a period of time of about 40 to 60 seconds, so that there is caused a great error in the measurement. In the embodiment of the present invention, the sample path has the lower horizontal part 34, which serves to suppress the undesired falling down of the reference electrode solution into the ion-selective electrode 14. Therefore, the length of the line between the open end 6 of the path 9 and the ion-selective electrode 14 may be rather short. This short length gives such an advantage that a saving of the amount of the blood sample employed can be accomplished. The amount of the sample employed in this embodiment of the present invention is at most 100 $\mu$l. The crank path in the cell body 1 may have a small volume of at most 13 $\mu$l.

The concentration of potassium ion in human whole blood is generally about 5 mmol. If the measurement error is allowed within about 0.1 mmol, the undesirable falling of the aqueous potassium chloride solution even in an amount of 1/10,000 of the total amount thereof is not allowable. Furthermore, if the path 9 for the reference electrode solution shown in FIG. 2 would not be horizontal but would be inclined towards the reference electrode 2, then it would be probable that the blood sample flows down from the sample outlet tube 13 and reaches the permeable membrane 8, so that a salt bridge cannot be formed.

The flow-through cell according to the embodiment of the present invention is so designed that the crank path has the upper horizontal part 35 and that the path 9 for the reference electrode solution is horizontal, and therefore i is possible to suppress the undesirable flowing of the blood cells contained in the sample from the outlet tube 13 to the reference electrode 2, even if there is a pressure variation in this system. Furthermore, in this embodiment, the turning portions each of the crank path have a curved area, so that any disturbance of the stream in the path can be effectively suppressed, and, in addition, the occurrence of bubbles can be greatly suppressed. Even if such bubbles should occur, they may be smoothly withdrawn.

The cell body 1 according to the embodiment of the present invention can be formed, for instance, by a method as mentioned below. A mold of the crank path integrated with the path 9 for the reference electrode solution is prepared. This mold is charged with a fusible alloy such as a bismuth-lead-tin alloy, having a melting point of about 90° C., to form a rod-like member having the same shape as that of the paths. The rod-like member is fixed to a mold of the cell body 1, and a plastic molding operation is carried out to form the cell body 1. The cell body product thus obtained is heated to melt the alloy enclosed therein and the resulting molten alloy is withdrawn from the cell body product. In the manner shown above, the desired paths in the cell body can be formed. The internal walls of these paths formed in this manner are very smooth like a mirror surface and have a very small roughness. Therefore, it is very rare for small bubbles to stagnate on such smooth walls.

What we claim is:

1. A flow-through cell provided with a reference electrode, comprising:

a cell body, having a sample path extending therethrough from a lower surface of the cell at an inlet to an upper surface of the cell at an outlet, the sample path having a crank path configuration including an upper horizontal part, a lower horizontal part, a first vertical part that communicates with each of said upper and lower horizontal parts, a second vertical part that communicates with the inlet and the lower horizontal part; and a third vertical part that communicates with the upper horizontal part and the outlet;

a reference electrode directly connected to a side of the cell body, the cell body having a path for a reference electrode solution, and said reference electrode having a bore wherein the path of the reference electrode solution is coaxially disposed with respect to the bore at one end thereof and is open at a middle portion of the first vertical part of the crank path at the other end, and further wherein the path for the reference electrode solution extends substantially horizontally through the cell body;

means for pumping disposed downstream of the cell body outlet for withdrawing liquid from the cell body through the outlet; and an ion-selective electrode directly connected to the lower surface of the cell body at the inlet.

2. A flow-through cell according to claim 1, wherein the horizontal and vertical portions of the crank path are connected along turning portions, each having a curved shape.

* * * * *